United States Patent
Mead et al.

(10) Patent No.: US 10,845,362 B2
(45) Date of Patent: Nov. 24, 2020

(54) COMPETITION ASSAY

(75) Inventors: Graham Peter Mead, Birmingham (GB); Hugh Carr Smith, Birmingham (GB); Arthur Randall Bradwell, Birmingham (GB)

(73) Assignee: THE BINDING SITE GROUP LIMITED, Birmingham (GB)

( * ) Notice: Subject to any disclaimer, the term of this patent is extended or adjusted under 35 U.S.C. 154(b) by 1725 days.

(21) Appl. No.: 13/810,777

(22) PCT Filed: Jul. 19, 2011

(86) PCT No.: PCT/GB2011/051353
§ 371 (c)(1),
(2), (4) Date: Apr. 15, 2013

(87) PCT Pub. No.: WO2012/010881
PCT Pub. Date: Jan. 26, 2012

(65) Prior Publication Data
US 2013/0217149 A1 Aug. 22, 2013

(30) Foreign Application Priority Data
Jul. 19, 2010 (GB) .................................. 1012049.1

(51) Int. Cl.
*G01N 33/53* (2006.01)
*G01N 33/68* (2006.01)
*G01N 33/543* (2006.01)

(52) U.S. Cl.
CPC ... *G01N 33/5306* (2013.01); *G01N 33/54313* (2013.01); *G01N 33/6857* (2013.01)

(58) Field of Classification Search
CPC ......... G01N 33/54313; G01N 33/6854; G01N 33/54366; G01N 33/543; G01N 33/551; G01N 33/53; G01N 33/5306; G01N 2021/825; G01N 21/274; G01N 21/4133; G01N 21/4738; G01N 21/4788; G01N 21/82; G01N 33/68
See application file for complete search history.

(56) References Cited

U.S. PATENT DOCUMENTS

| | | |
|---|---|---|
| 3,907,502 A | 9/1975 | Brink |
| 4,444,879 A | 4/1984 | Foster et al. |
| 4,618,589 A | 10/1986 | Jefferis et al. |
| 4,791,067 A * | 12/1988 | Sheiman et al. .............. 436/513 |
| 4,792,529 A | 12/1988 | Rudick et al. |
| 4,983,530 A | 1/1991 | Carlson |
| 5,185,066 A | 2/1993 | Golias et al. |
| 8,227,201 B2 | 7/2012 | Cooke et al. |
| 2002/0182748 A1 | 12/2002 | Reardon |
| 2004/0018576 A1 | 1/2004 | DeMatteo et al. |
| 2008/0166742 A1* | 7/2008 | Bradwell .................... 435/7.92 |
| 2009/0068677 A1 | 3/2009 | Matsumori et al. |
| 2009/0274704 A1 | 11/2009 | Kim |

FOREIGN PATENT DOCUMENTS

| | | |
|---|---|---|
| DE | 202004012479 | 11/2004 |
| EP | 0044219 | 1/1982 |
| EP | 0336472 | 6/1993 |
| EP | 0291194 | 2/1994 |
| EP | 1870710 | 12/2007 |
| GB | 2472518 | 2/2011 |
| JP | S63-139199 | 6/1988 |
| JP | M03-199966 | 8/1991 |
| WO | WO1997/017372 | 5/1997 |
| WO | WO2005/103717 | 11/2005 |
| WO | WO2005/116651 | 12/2005 |
| WO | WO2007/125338 | 11/2007 |
| WO | WO2006/079816 | 8/2009 |
| WO | WO2009095665 | 8/2009 |
| WO | WO 2010049672 A2 * | 5/2010 ............. G01N 33/53 |
| WO | WO2010/049672 | 7/2010 |
| WO | WO2011/021041 | 4/2011 |

OTHER PUBLICATIONS

Tate et al. ("Quantitative Serum Free Light Chain Assay—Analytical Issues" Clin Biochem Rev vol. 30 Aug. 2009).*
Murata et al. ("Sharply Increased Serum Free Light-Chain Concentrations after Treatment for Multiple Myeloma" Clinical Chemistry 56:1 16-20 , 2010).*
Bradwell et al. ("Highly Sensitive, Automated Immunoassay for Immunoglobulin Free Light Chains in Serum and Urine" Clinical Chemistry 47:4 673-680 (2001)).*
Thakkar et al. ("Development and validation of a particle-enhanced turbidimetric inhibition assay for urine albumin on the Dade aca analyzer" Clinical Chemistry 43:1, 109-113 (1997) Automation and Analytical Techniques).*
GenWay Biotech ("Affinity Purified Anti-MOUSE (Kappa Chain) (RABBIT)" GenWay Biotech, Inc.), and Bradwell et al. ("Highly Sensitive, Automated Immunoassay for Immunoglobulin Free Light Chains in Serum and Urine" Clinical Chemistry 47:4 673-680 (2001)) (Hereinafter Bradwell (2001) ).*
Bangs Laboratories. ("Light-Scattering Assays—TechNote 304" Bangslabs.com, 1998).*
te Velthuis et al. ("N latex FLC—new monoclonal high-performance assays for the determination of free light chain kappa and lambda" Clin Chem Lab Med 2011;49(8):1323-1332).*
Campbell et al. ("Development of a highly-sensitive multi-plex assay using monoclonal antibodies for the simultaneous measurement of kappa and lambda immunoglobulin free light chains in serum and urine" Journal of Immunological Methods vol. 391, Issues 1-2, May 31, 2013, pp. 1-13).*

(Continued)

Primary Examiner — Changhwa J Cheu
(74) Attorney, Agent, or Firm — Barnes & Thornburg LLP

(57) ABSTRACT

The application provides competition assays used to detect free-light chains or intact immunoglobulins comprising incubating the sample with anti-FLC antibody, or heavy chain class-light chain type-specific antibodies, or fragments of such antibodies, and a known amount of FLC or intact immunoglobulin and detecting the binding of the antibody to the known amount of FLC or immunoglobulin. Assay kits and methods of producing particles coated with FLC are also provided.

9 Claims, 5 Drawing Sheets

(56) References Cited

OTHER PUBLICATIONS

Yadav et al. ("The use of immunoglobulin light chain assays in the diagnosis of paraprotein-related kidney disease" Kidney International (2015) 87, 692-697; doi:10.1038/ki.2014.333).*
Bradwell et al. ("Assessment of Monoclonal Gammopathies by Nephelometric Measurement of Individual Immunoglobulin / Ratios" Clin Biochem Rev vol. 30 Aug. 2009).*
Ling et al. ("Detection of free kappa chains in human serum and urine using pairs of monoclonal antibodies reacting with C kappa epitopes not available on whole immunoglobulins" Clin Exp Immunol. Apr. 1983; 52(1): 234-240).*
Roche (Turbidimetric inhibition immunoassay (TINIA) for the in vitro determination of hemoglobin A1c in whole blood or hemolysate Roche Diagnostics Ltd. CH-6343 Rotkreuz Switzerland).*
Emond et al. ("Aggregation of Serum Free Light Chains (FLC) Causes Overestimation of FLC Nephelometric Results as Compared to Serum Protein Electrophoresis (SPE) While Preserving Clinical Usefulness" Blood (ASH Annual Meeting Abstracts) 2007 110: Abstract 4767).*
Darwish (International Journal of Biomedical Science Year 2006 p. 217-235) (Year: 2006).*
Nolan et al. (Cytometry A 2006 69:318-325). (Year: 2006).*
Kumar, S, et al., "Serum immunoglobulin free light-chain measurement in primary amyloidosis: prognostic value and correlations with clinical features," Blood 116(24): 5126-5129 (Dec. 9, 2010).
Borde J P, et al., "Kappa-light chain amyloidosis of the liver, a rare cause of liver enzyme elevation," Deutsche Medizinische Wochenschrift, 133(21):1116-1120 (May 1, 2008).
Preud'Homme J L, et al., "Synthesis of abnormal heavy and light chains in multiple myeloma with visceral deposition of monoclonal immunoglobulin," Clinical and Experimental Immunology, 42(3):545-553 (Dec. 1, 1980).
Hannam-Harris, A C, et al., "Free immunoglobulin light chain synthesis by human foetal liver and cord blood lymphocytes," Immunology, 43(3): 417-423 (Jul. 1, 1981).
PCT International Search Report and Written Opinion for PCT/GB2011/050518 dated May 17, 2011.
PCT International Search Report for PCT/IB2011/050919 dated Aug 10, 2011.
Hutchison, C A, et al., "Quantitative assessment of serum and urinary polyclonal free light chains in patients with chronic kidney disease," Clinical Journal of the American Society of Nephrology, 3(6):1684-1690 (Nov. 1, 2008).
Bhawna Sirohi "Serum Free Light Chain Assessment in Myeloma Patients Who Are in Complete Remission by Immunofixation," Blood 100(11): Abstr. (Nov. 16, 2002).
Hutchison, C A, et al., "Monoclonal Gammopathy as a Determinant of Adverse Outcomes in Patients with Chronic Kidney Disease," Blood (ASH Annual Meeting Abstracts) 108: Abstract 5053 (2006).
Hutchison, C A, et al., "Serum free light chain assessment in monoclonal gammopathy and kidney disease," Nature Reviews Nephrology, 5: 621-628 (Nov. 2009).
Bergner, R, et al., "Free light chains in urine—an additional diagnostic advantage?" Nephrol. Dial. Transplant. 22(suppl 6): vi66-vi67, abstract FP145 (Jun. 22, 2007).
Katzmann, J A, et al., "Serum Reference Intervals and Diagnostic Ranges for Free κ and Free λ Immunoglobulin Light Chains: Relative Sensitivity for Detection of Monoclonal Light Chains," Clinical Chemistry 48(9): 1437-1444 (2002).
Levinson, S, et al., "Hook effect with lambda free light chain in serum free light chain assay," Clinica Chimica Acta 411(21-22): 1834-1836 (Nov. 11, 2010).
Ling, N R, et al., "Attachment of antigens and antibodies to fixed red cells; Their use in rosette and haemagglutination tests; A comparison with fresh red cells," Molecular Immunology 16(9): 637-642 (Sep. 1979).
Lowe, J, "Properties of monoclonal antibodies to human immunoglobin kappa and lambda chains," Immunology 42: 649-659 (1981).

Gartner, A, et al., "A Microparticle Enhanced Nephelometric Immunoassay (Nephelia$^R$) Applied to Thymulin Measurement," Journal of Immunoassay, 12(4): 521-542 (1991).
Nishikawa, T, et al., "Competitive Nephelometric Immunoassay of Carbamazepine and its Epoxide Metabolite in Patient Blood Plasma," J Pharmacobiodyn, 4(1): 77-83 (Jan. 1981).
Koo, K, et al., "Development of a Streptavidin-Conjugated Single-Chain Antibody That Binds *Bacillus cereus* Spores," Applied and Environmental Microbiology, 64(7): 2497-2502 (Jul. 1998).
Daval, S, et al., "Risk of Antigen Excess in Serum Free Light Chain Measurements ," Clinical Chemistry, 53(11): 1985-1992 (Nov. 2007).
Thakkar, H, et al., "Development and validation of a particle-enhanced turbidimetric inhibition assay for urine albumin on the Dade aca® analyzer," Clinical Chemistry, 43(1):109-113 (Jan. 1997).
Parant, F, et al., "Hydroxyzine and Metabolites as a Source of Interference in Carbamazepine Particle-Enhanced Turbidimetric Inhibition Immunoassay (PETINIA)," Therapeutic Drug Monitoring, 27(4): 457 (Abstract) (Aug. 2005).
Merck Millipore: Estapor® White Microspheres, A critical raw material for the manufacture of IVD and life science reagents, EMD Merck Millipore, Billerica, MA (2012).
Bence Jones Protein Dipstick Rapid Test, Competitive immunochromatographic test for the detection of free light chains κ and λ in urine, Globe Diagnostics S.r.l., Milan, Italy (Dec. 18, 2007).
Grange, J., et al., "Nephelometric assay of antigens and antibodies with latex particles," Journal of Immunological Methods, 18(3-4): 365-375 (Dec. 1977).
Bangs Laboratories, Tech Note #304: Light Scattering Assays. Bangs Laboratories, Fishers, IN Rev. #003 (Mar. 20, 2013).
Cobas, Tina-quant® HbA1c Gen. 3: Turbidimetric inhibition immunoassay (TINIA) for the in vitro determination of hemoglobin A1c in whole blood or hemolysate, Roche Diagnostics Ltd, Rotkreuz, Switzerland (2013).
Bakkeren, D L, et al., "Multicenter Evaluation of an Improved Immunoturbidimetric Assay for the Determination of HbA1c on Clinical Chemistry Analyzers," Clin. Lab., 45: 123-137 (Abstract) (1999).
Gotelli, G, et al., "Particle-Enhanced Turbidimetric Inhibition Immunoassay for Theophylline with a Centrifugal Analyzer," Clinical Chemistry 31(6):1065-1066 (Jun. 1985).
Bradwell et al., "Highly Sensitive, Automated Immunoassay for Immunoglobulin Free Light Chains in Serum and Urine," Clinical Chemistry, 2001, vol. 47 No. 4 pp. 673-680.
Marshall, G., et al., "Borderline High Serum Free Light Chain [kappa]/[lambda] Ratios Are Seen Not Only in Dialysis Patients but Also in Non-Dialysis-Dependent Renal Impairment and Inflammatory States," Aug. 2009, American Journal of Clinical Pathology, vol. 132, No. 2, p. 308-309.
Landgren et al., "Monoclonal gammopathy of undetermined significance (MGUS) consistently precedes multiple myeloma: a prospective study," Blood, 113(22): 5412-5417 (May 28, 2009).
United Kingdom Search Report completed Oct. 4, 2010, for corresponding United Kingdom Patent Application No. GB1013891.5.
PCT Search Report and Written Opinion, prepared for PCT/GB20101051373 dated Feb. 10, 2011.
Examination Report Under Section 18(3) completed Apr. 11, 2011, for corresponding United Kingdom Patent Application No. GB1013891.5.
Notification of Grant completed Oct. 18, 2011, for corresponding United Kingdom Patent Application No. GB1013891.5.
Abadie, Jude M., et al., "Are Renal Reference Intervals Required When Screening for Plasma Cell Disorders With Serum Free Light Chains and Serum Protein Electrophoresis," Am. J. Clin. Pathol., No. 131, pp: 166-171 (2009).
Abe, M., et al., "Differences in Kappa to Lambda Ratios of Serum and Urinary Free Light Chains", Clin. Exp. Immunology, No. 111, pp: 457-462 (1998).
Li Bricon, T, et al., "Urinary free light chain analysis by the Freelite® immunoassay: a preliminary study in multiple myeloma," 35(7): 565-567 (Oct. 2002).

(56) References Cited

OTHER PUBLICATIONS

Bruck, P, et al., "Lambda- and kappa-free light chains in haematologic patients," Clinical Exp. Med; 49(1): 19-22 (2008).
Gertz, Morie A., et al., "Hepatic Amyloidosis: Clinical Appraisal in 77 Patients," Hepatology, 25(1) : 118-121 (1997).
Hofmann, "A new concept for detection of Bence Jones proteinuria in patients with monoclonal gammapathy," Clin. Lab., 50(3-4):181-5 (2004).
Hooper, J E, et al., "Clinical relapse in systemic lupus erythematosus: correlation with antecedent elevation of urinary free light-chain immunoglobulin," J Clin Immunol., 9(4):338-50 (Jul. 1989).
Hutchison, C A, et al., "Quantitative assessment of serum and urinary polyclonal free light chains in patients with type II diabetes: an early marker of diabetic kidney disease?" Expert Opin Ther Targets. 12(6):667-76 (Jun. 2008).
Jefferis R. et al, "Quantitation Of Human Total IgG, Kappa IgG and Lambda IgG In Serum Using Monoclonal Antibodies," Journal Of Immunological Methods, 39(4):355-362 (Dec. 1980).
Kyrtsonis, M. et al, "Serum free light chain ratio (FLCR) at diagnosis constitutes powerful prognostic factor for survival of multiple myeloma (MM)," Blood, (ASH Annual Meeting Abstracts), No. 108 (2006).
Rajkumar S. Vincent, et al., "Presence of Monoclonal Free Light Chains in Serum Predicts Risk of Progression in Monoclonal Gammopathy of Undetermined Significance (MGUS)," Blood, vol. 102, No. 11, Abstract (2003).
Ricotia, D., Serum Light Chains in Plasmacell Dyscrasias: Comparison of 2 Assays, Jun. 2007, XI Myeloma Conference, Greece.
Rossi, Jean Francois, et al., A Phase 1111 Study of Atacicept (TACI-Ig) To Neutralize APRIL and BLyS in Patients with Refractory or Relapsed Multiple Myeloma (MM) or Active Previously Treated Waldenstrom's Macroglobulinemia (WM), Blood, vol. 108, No. 3578, Abstract. (2006).
Staggs, Brent, "Comparison of Serum Quantitative Free Light Chains (Freelite) to Serum Quantitative Total Light Chains in Recurrent Multiple Myeloma," Arch. Pathol. Lab. Med., 128: 143 (2004).
The Binding Site Ltd Freelite Catalogue pages dated Mar. 10, 2011.
PCT Search Report and Written Opinion prepared for PCT/GB2011/050197, dated Mar. 16, 2011.
Fagnart, O.C., et al., "Free Kappa and Lambda Light Chain Levels in the Cerebrospinal Fluid of Patients With Multiple Sclerosis and Other Neurological Diseases", Journal of Neuroimmunology, 19(1-2):119-132 (Jan. 1988).
PCT Search Report and Written Opinion prepared for PCT/GB2011/050193, dated Mar. 16, 2011.
Bradwell, A., "Clinical Applications of Serum Free Light Chain Immunoassays," Clinical Laboratory International, Pan European Publishing, pp: 1-4 (Nov. 2003).
Finney et al., "Initial evaluation of cystatin C measurement by particle-enhanced immunonephelometry on the Behring nephelometer systems," Clinical Chemistry, 43(6):1016-1022 (1997).
Koenig et al., "Plasma concentratios of Cystatin C in Patients with Coronary Heart Disease and Risk for Secondary Cardiovascular Events," Clinical Chemistry 51(2): 321-327 (2005).
Sanchorawala, "Light-Chain (AL) amyloidosis: Diagnosis and Treatment," Clinical Journal of the American Society of Nephrology, 1:1331-1341, (2006).
Tate et al., "Quantitative Serum Free Light Chain Assay—Analytical Issues," Clin Biochem Rev, 30:131-140 (Aug. 2009).
Lidgerding, B, "Determination of Class and Subclass of Mouse Monoclonal Antibodies by ELISA," J tissue Culture Methods, 12(3):111-114 (1989).
Mayumi et al, "Studies on the clonal origin of human B cell leukemia using monoclonal anti-idiotype antibodies," The Journal of Immunology, 129(2):904-910 (Aug. 1, 1982).
Koziner et al, "Characterization of B-cell leukemias: a tentative immunomorphological scheme," Blood, 56:815-823 (Nov. 1, 1980).
Freedman et al, "Normal cellular counterparts of B cell chronic lymphocytic leukemia," Blood, 70(2):418-427 (Aug. 1, 1987).
Vaandrager et al, "DNA Fiber Fluorescence In Situ Hybridization Analysis of Immunoglobulin Class Switching in B-Cell Neoplasia: Aberrant CH Gene Rearrangements in Follicle Center-Cell Lymphoma," Blood, 92(8):2871-2878 (Oct. 15, 1998).
Boorsma, "Direct immunoenzyme double staining applicable for monoclonal antibodies," Histochemistry, 80(2):103-106 (1984).
Borche et al, "Evidence that chronic lymphocytic leukemia B lymphocytes are frequently committed to production of natural autoantibodies," Blood, 1990, 76(3):562-569 (Aug. 1, 1990).
Fine et al, "Waldenström's Macroglobulinemia in Monozygotic Twins," Acta Med Scand 1986, 220(4): 369-73 (1986).
Sun et al, "Bcl-2 and Bcl-xL Inhibit CD95-mediated Apoptosis by Preventing Mitochondrial Release of Smac/DIABLO and Subsequent Inactivation of X-linked Inhibitor-of-Apoptosis Protein," J Biol Chem, 277:11345-11351 (Mar. 29, 2002).
Kearney et al, "A New Mouse Myeloma Cell Line that Has Lost Immunoglobulin Expression but Permits the Construction of Antibody-Secreting Hybrid Cell Lines," J Immunology, 1979, 123(4):1548-1550 (Oct. 1, 1979).
Borup-Christensen et al, "Human-human hybridomas for the study of anti-tumor immune response in patients with colorectal cancer," (Int J Cancer, 37(5):683-688 (May 15, 1986).
Dawson et al, "Monoclonal antibodies to hepatitis A virus," J Medical Virology, 14(1):1-8 (1984).
Shimizu, M., "Ratio of κ/λ light chain of IgD in sera of healthy individuals and its significance," Acta Medica, (1981) 37(1) 179-188.
Prior M. et al, "Quantitation Of IgGkappa And IgGlambda In Normal And Pathological Sera," Protides Of The Biological Fluids, 29:785-788 (1981).
Derverill et al, "Monoclonal Antibodies To Human IgG: Reaction Characteristics In The Centrifugal Analyzer," Clinical Chemistry, vol. 27(12):2044-2047 (1981).
International Search Report and Written Opinion for PCT/GB2006/000267 filed May 24, 2006.
Abraham, R.S., et al., "Light Chain Myeloma: Correlation of Serum Nephelometric Analysis For the Quantitation of Immunoglobulin Free Light Chain With urine Bence Jones Protein" (abstract) presented at AACC Chicago, IL 2001, Clinical Chemistry, vol. 47, No. S6, pp. A33.
Anonymous: "Serum and Urine Protein Electrophoresis (SPE/UPE", Internet Article, Oct. 12, 2004, URL:http://web.archive.org/web/20041012055838/http://www.bindingsite.co.uk/electrophoresis.asp.
Bradwell, Arthur R., et al., "Serum Free Light Chain Immunoassays and Their Clinical Application", 2002, Clinical and Applied Immunology Reviews, vol. 3, pp. 17-33.
Bradwell, Arthur R., et al., "Serum Test for Assessment Of Patients With Bence Jones Myeloma", Feb. 8, 2003, The Lancet (Reprint), vol. 361, No. 9356, pp. 489-491.
Bradwell, Arthur R., "Serum Free Light Chain Analysis", 2004, 2nd Edition, The Binding Site Ltd., , ISBN: 07044 24541, pp. 15-16 Fig. 3.4 on p. 16, and Text on p. 15.
Bradwell, Arthur R., "Serum Free Light Chain Analysis", 2004, 2nd Edition, The Binding Site Ltd., , ISBN: 07044 24541, Chapters 4, 5, and 6, pp. 23-62.
Chui, Shiu Hon, et al., "Light-Chain Ratio of Serum IgA1 in IgA Nephropathy", 1991, Journal Of Clinical Immunology, vol. 11, No. 4, pp. 219-223.
Haraldsson, A., et al., "Determination Of Kappa And Lambda Light Chains In Serum Immunoglobulins G, A and M", 1991, Ann. Clin. Biochem, vol. 28, pp. 461-466.
Drayson, Mark, et al., "Serum Free Light-Chain Measurements For Identifying And Monitoring Patients With Nonsecretory Multiple Myeloma", May 1, 2001, Blood, vol. 97, No. 9, pp. 2900-2902.
Lachmann, Helen J., et al., "Outcome in Systemic AL Amyloidosis In Relation To Changes In Concentration Of Circulating Free Immunoglobulin Light Chains Following Chemotherapy", 2003, British Journal Of Haematology, vol. 122, pp. 78-84.
Mead, G.P., et al., "Serum Free Light Chain Immunoassays As An Aid In The Diagnosis And Monitoring Of Light Chain Monoclonal Gammopathies", Oct. 2001, pp. 239 (abstract) Proceedings of the Joint Annual Meeting of HSANZ and ASBT.

(56) References Cited

OTHER PUBLICATIONS

Mead, G.P., et al., "Nephelometric Measurement Of Serum Free Light Chains in Nonsecretory Myeloma", 2002, Clin Chem, vol. 48, No. 6 (abstract), Presented at the AACC, FL.

Mead, G.P., et al., "Serum Free Light Chains For Monitoring Multiple Myeloma", 2004, Blackwell Publishing Ltd, British Journal of Haematology, vol. 126, pp. 348-354.

Nakano, Takanari, et al., "ELISAs For Free Human Immunoglobulin Light Chains In Serum: Improvement Of Assay Specificity By Using Two Specific Antibodies In A Sandwich Detection Method", Journal Of Immunological Methods, 293: 183-189 (2004).

Sirohi, Bhawana, et al., "Multiple Myeloma", The Lancet, vol. 363: 875-887 (2004).

Chersi et al., "Polystyrene Beads Coated with Antibodies Directed to HLA Class I Intracytoplasmic Domain: The Use in Quantitiative measurement of Peptide-HLA Class I binding by Flow Cytometry,", Human Immunology, 61; 1298-1306 (2000).

Whicher et al., "Use of Immunoglobulin Heavy- and Light-Chain Measurements Compared with Existing Techniques as a Means of Typing Monoclonal Immunoglobulins," Clin. Chem., 33(10): 1771-1773 (1987).

Beaume et al., "High Incidence of Serum Monoclonal Igs Detected by a Sensitive Immunoblotting Technique in B-Cell Chronic Lymphocytic Leukemia," Blood, 84(4): 1216-1219 (1994).

Jones et al., "Use of Immunoglobuliln Heavy-Chai and Light-Chain Measurements in a Multicenter Trial to Investigate Monoclonal Components: II. Classification by use of Computer-Based Algorithms," Clin. Chem., 37(11): 1922-1926 (1991).

Shimizu et al., "Differentiation of benign monoclonal gammopathy and smouldering multiple myeloma from frank myeloma," Clin. Exp. Immunol., 50: 596-600 (1982).

Briault et al., "Isotypy of serum monoclonal immunoglobulins in human immunodeficiency virus-infected adults," Clin. Exp. Immunol., 74: 182-184 (1988).

Pappas et al., "Reduced False Positive Reactions in the Dot-Enzyme-Linked Immunosorbent Assay for Human Visceral Leishmaniasis," Clin. Immunol. Immunopathology, 34: 392-396 (1985).

Chui et al., "Light-Chain Ratios of Immunoglobulins G, A, and M Determined by Enzyme Immunoassay," Clin. Chem. 36(3): 501-502 (1990).

Samoszuk et al., "Enzyme Immunoassay for Detection of Monoclonal Immunoglobulin in Lymph Nodes," Cancer, vol. 60(11): 2726-2721 (1987).

Cohen et al. "Free Immunoglobulin Light Chains as a Risk Factorin Renal and Extrarenal Complications" Seminars in Dialysis, vol. 22, No. 4. pp. 369-372 (2009).

Cohen et al. "Immunoglobulin light chains in uremia" Kidney International, vol. 63, Supplement 84, pp. S15-S18 (2003).

Blade et al. "Renal, hematologic and infectious complications in multiple myeloma", Best Practice & Research Clinical Haematology, vol. 18, No. 4, pp. 635-652, (2005).

Nakano et al. "Immunochemical quantification of free immunoglobulin light chains from an analytical perspective" Clin Chem Lab Med; 44(5): 522-532 (2006).

Davern et al. "Immunodiagnostic Capabilities of Anti-Free Immunoglobulin Light Chain Monoclonal Antibodies" Am J Clin Pathol.; 130(5): 702-711 (Nov. 2008).

Pratt et al. "The evolving use of serum free light chain assays in haematology," British Journal of Haematology, 141, 413-422, (Mar. 3, 2008).

Nakano et al. ("Free immunoglobulin light chain: Its biology and implications in diseases" Clinica Chimica Acta 412: 843-849 (2011).

Mayeux et al. "Biomarkers: Potential uses and Limitations"; NeuroRx; vol. 1, pp. 182-188 (2004).

Soiling et al. "Free Light Chains of Immunoglobulins in Serum from Patients with Rheumatoid Arthritis, Sarcoidosis, Chronic Infections and Pulmonary Cancer" Acta medica Scandinavica, 209(6): 473-477 (2009).

\* cited by examiner

Figure 6
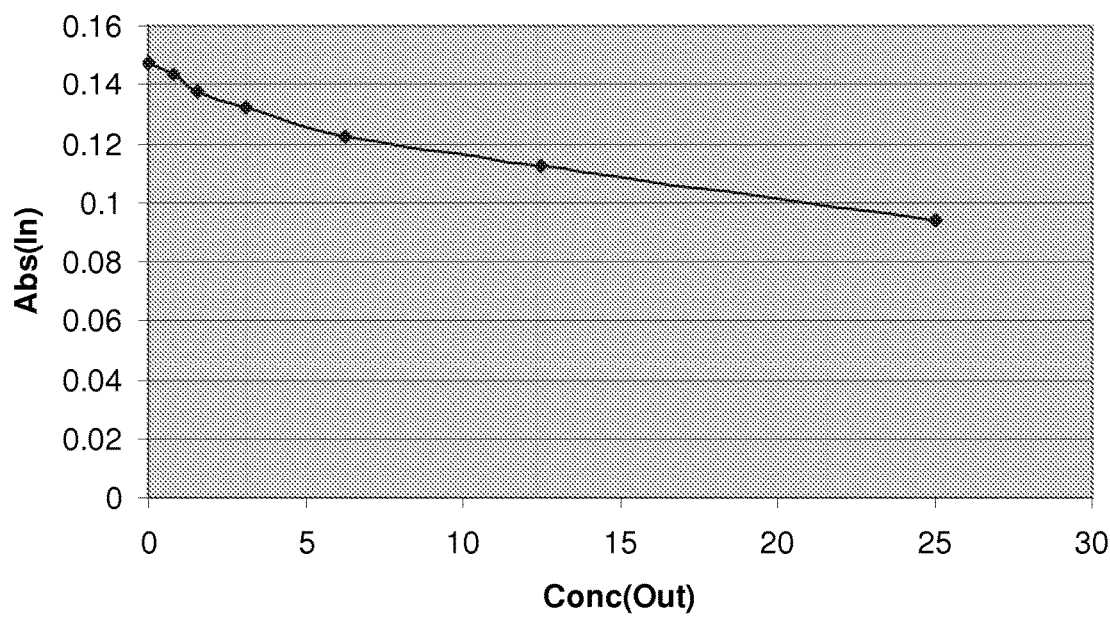
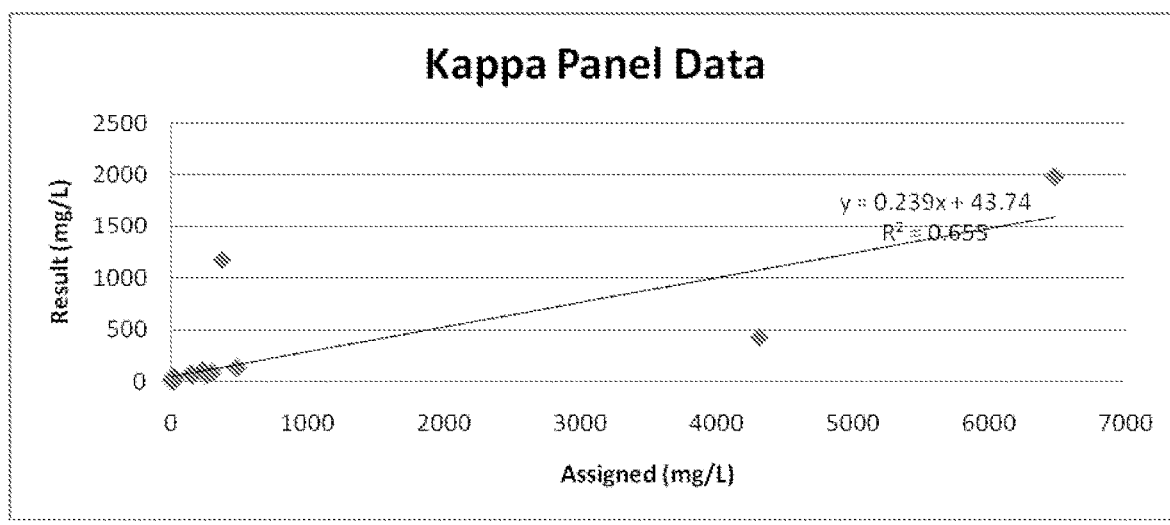
Figure 7

Figure 8
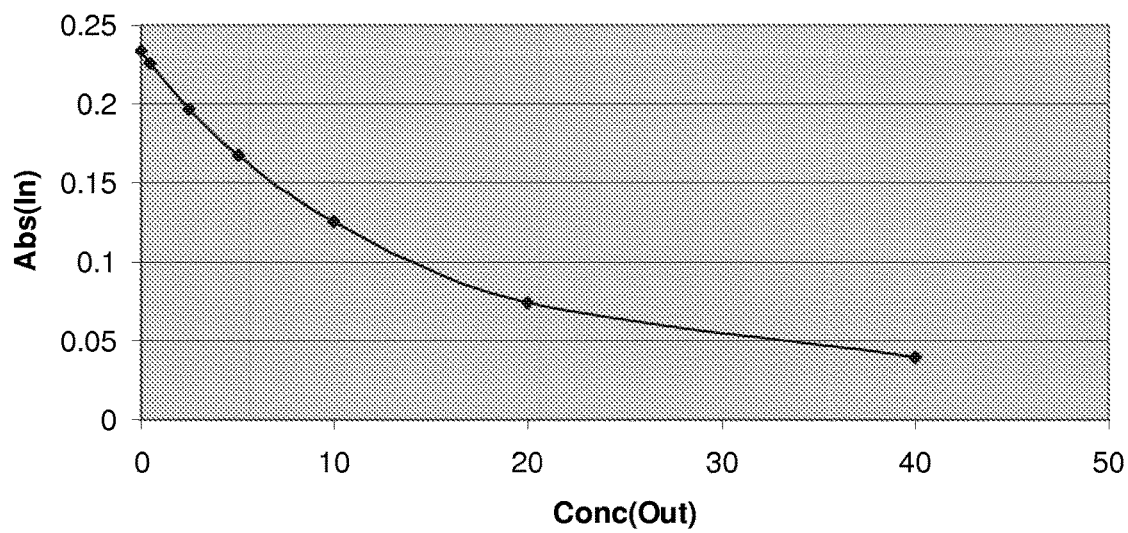
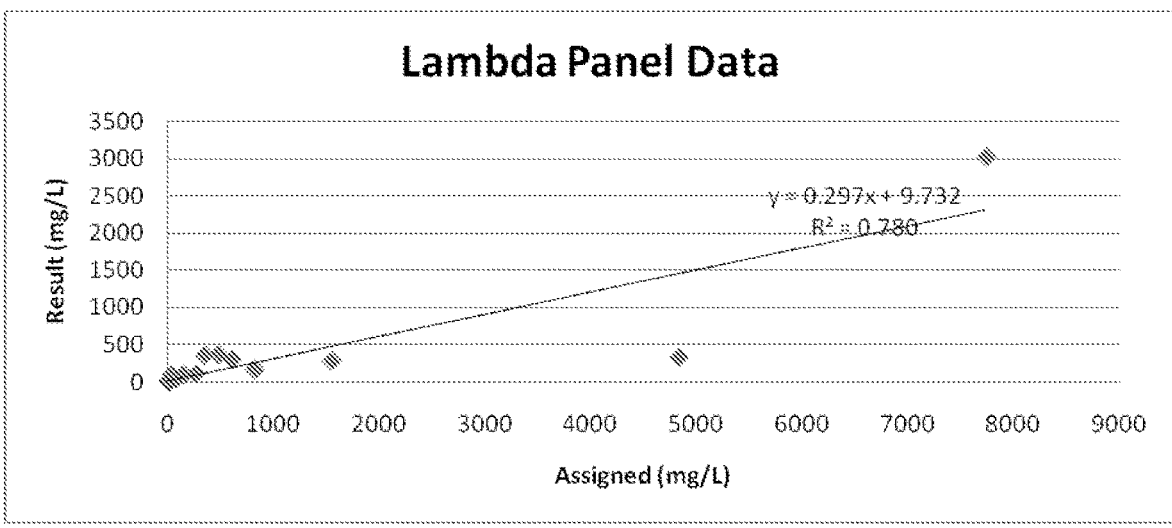
Figure 9

COMPETITION ASSAY

CROSS REFERENCE TO RELATED APPLICATIONS

This application is a U.S. national counterpart application of International Application No. PCT/GB2011/051353, filed Jul. 19, 2011, which claims priority to G.B. Patent Application No. 1012049.1, filed Jul. 19, 2010. The entire disclosures of PCT/GB2011/051353 and G.B. Patent Application No. 1012049.1 are hereby incorporated by reference.

The invention relates to improved turbidimetric and nephelometric assays for serum Free Light Chains (sFLC) and kits for such assays.

Nephelometric assays have been used for several years to assay for sFLC. They are used to diagnose and monitor monoclonal gammopathies, such as light chain multiple myeloma.

The term nephelometry is used to describe the measurement of light scattering by a substance, usually in suspension. The scattered light is measured using a detector placed at an angle relative to the incident light beam. Turbidimetry is the measurement of the amount of light lost by dispersion of an incident light beam as it passes through a substance. In this case, the loss of intensity of the incident beam is measured using a light detector directly in the light path as it emerges from the sample. Both of these photometric methods yield similar results and the following discussion can be applied equally to either.

Immunoassays are based on measuring the reaction between a protein (antigen) and an antibody specific to that protein. One antibody is able to bind to two antigen particles and an antigen may be bound by more than one antibody, allowing large immune complexes of cross-linked antibody/antigen to be formed. A nephelometric/turbidimetric immunoassay is a liquid phase test in which a solution of antigen (usually in the form of serum, plasma or urine) is mixed with a solution of antibody. As the reaction proceeds, the immune complexes become progressively less soluble and eventually precipitate out of solution. The precipitated particles scatter light much more efficiently than the separate protein molecules leading to an increase in both cloudiness (turbidity) and light scattering. In general, assuming a fixed concentration of antibody (in excess), a higher concentration of antigen in the reaction mixture leads to a larger increase in scattered light, forming the basis of a quantitative assay.

Typical nephelometric/turbidimetric immunoassays have a sensitivity limit of approximately 100 mg/l. The sensitivity of the assay can be improved through the use of latex enhancement. Antibody molecules are attached to particles such as polystyrene spheres which have a diameter in the order of hundreds of nanometres. These particles are more efficient at scattering light and become progressively more so as the attached antibodies react with their antigens. Use of these particles can lead to a 10- to 100-fold increase in sensitivity of nephelometric/turbidimetric assays.

Antibody molecules (also known as immunoglobulins) have a twofold symmetry and are composed of two identical heavy chains and two identical light chains, each containing variable and constant domains. The variable domains of the heavy and light chains combine to form an antigen-binding site, so that both chains contribute to the antigen-binding specificity of the antibody molecule. The basic tetrameric structure of antibodies comprises two heavy chains covalently linked by a disulphide bond. Each heavy chain is in turn attached to a light chain, again via a disulphide bond. This produces a substantially "Y"-shaped molecule.

Heavy chains are the larger of the two types of chain found in antibodies, with typical molecular mass of 50,000-77,000 Da, compared with the smaller light chain (~25,000 Da).

There are five main classes of heavy chain which are $\gamma$, $\alpha$, $\mu$, $\delta$ and $\epsilon$ which are the constituent heavy chains for: IgG, IgA, IgM, IgD and IgE respectively. IgG is the major immunoglobulin of normal human serum, accounting for 70-75% of the total immunoglobulin pool. This is the major antibody of secondary immune responses. It forms a single tetramer of two heavy chains plus two light chains.

IgM accounts for approximately 10% of the immunoglobulin pool. The molecules, together with J-chains, form a pentamer of five of the basic 4-chain structures. The individual heavy chains have a molecular weight of approximately 65,000 and the whole molecule has a molecular weight of about 970,000. IgM is largely confined to the intravascular pool and is the predominant early antibody.

IgA represents 15-20% of the human serum immunoglobulin pool. More than 80% of IgA occurs as a monomer. However, some of the IgA (secretory IgA) exists as a dimeric form.

IgD accounts for less than 1% of the total plasma immunoglobulin.

IgE, although scarce in normal serum, is found on the surface membrane of basophils and mast-cells. It is associated with allergic conditions such as asthma and hay-fever.

In addition to the five main classes, there are four sub-classes for IgG (IgG1, IgG2, IgG3 and IgG4). Additionally there are two subclasses for IgA (IgA1 and IgA2).

There are two types of light chain: Lambda and Kappa. There are approximately twice as many kappa as lambda molecules produced in humans, but this is quite different in some mammals. Each chain contains approximately 220 amino acids in a single polypeptide chain that is folded into one constant and one variable domain. Plasma cells produce one of the five heavy chain types together with either kappa or lambda molecules. There is normally approximately 40% excess free light chain production over heavy chain synthesis. Where the light chain molecules are not bound to heavy chain molecules, they are known as "free light chain molecules (FLC)". The kappa light chains are usually found as monomers. The lambda light chains tend to form dimers.

Nephelometric assays have been produced for FLC. Such assays use anti-FLC antibodies. They are commercially available, for example under the trademark "Freelite" from The Binding Site, Birmingham, UK Antibodies which are heavy chain class-light chain type specific are also known in the art. See for example WO 2006079816, and sold under the Trademark "Hevylite" by The Binding Site.

As a consequence of the wide range of sFLC (serum free light chain) concentrations that may be encountered, the variable nature of the monoclonal proteins and the limited number of specific epitopes that may be available for antibody binding, the assays do have certain analytical shortcomings:

Abraham R. S. et al (Clin. Chem. (2002) 48:10, 1805-1811) report the presence of trimeric complexes of $\lambda$ free light chains affecting nephelometric measurement. Daval S. et al (Clin. Chem. (2007) 53 (11) 1985-1986) discuss the identification of falsely low sFLC readings from patients with high sFLC concentrations determined via nephelometry. The authors of that paper recommend carrying out a dilution of the samples to ensure that antigen excess is not having an effect on the determination of sFLC in samples.

Briand P-Y. et al (Clin. Chem Lab Med (2010) 48(1)) reviewed the nephelometric-based assay "Freelite" (The Binding Site Group Limited, Birmingham, UK). This is acknowledged as a valuable tool for measuring sFLC, but the authors highlighted a number of limitations to the assay system. These included overestimation of some samples by nephelometry. The authors of the paper recommended rerunning some samples at different dilutions to improve the reproducibility of the assay.

Tate J. et al (Clin. Biochem. Rev. (2009) 30, 131-140 and Clin.Chem Acta (2007) 376, 30-36 raised similar issues in a small number of cases.

de Kat Angelino C. M. et al Clin. Chem (2010) 56:7 discuss the overestimation of κ serum free light chain (κ-sFLC) concentrations by immunonephelometry. The authors observed an overestimation of κ-sFLC in a patient with κ light chain myeloma using nephelometry. The authors then compared nephelometric assays with an ELISA-based assay for sFLC. The authors observed that higher concentrations of κ-sFLC had reduced accuracy when measured by nephelometry. ELISA produced estimates of κ-sFLC concentration closer to those indicated by densitometric measurement of serum protein electrophoresis gels. The authors of the paper speculated that κ-sFLC can spontaneously polymerise which influences nephelometric quantification of the κ-sFLC. The authors recommend using ELISA to quantify sFLC.

The Applicant believes that assaying sFLC produces a number of problems, not normally associated with nephelometric assays of proteins.

FLC are relatively small proteins of about 220 amino acids each, which present problems often not associated with larger proteins. They exist as lambda and kappa forms.

The antibodies used in commercial systems to detect sFLC bind to antigenic sites which are normally hidden when the light chain is bound to heavy chains in intact antibodies. There are thought to be relatively few antibody-binding sites (epitopes) on the small molecules. This is thought to make the sFLC more susceptible to antigenic excess and inconsistencies in the determination of concentrations.

Moreover, the formation of multimers of sFLC, such as κ-sFLC also raises difficulties for the nephelometric system used to assay the sFLC. The presence of polymeric κ-sFLC in samples can increase the rate of immune complex formation (during the assay) and lead to over-estimation of sFLC concentrations when compared to un-polymerised calibrators.

Assays using heavy chain class-light chain type-specific antibodies are also likely to suffer from similar difficulties. Monoclonal IgA is also known to form polymers. The antigenic sites to which the heavy chain class-light chain type-specific antibodies bind are also believed to be in a limited region of the immunoglobulins and are likely to be relatively few, so leading to similar problems to sFLC assays.

There is therefore a need to improve the consistencies and accuracy of nephelometric assays for sFLC or for measuring heavy chain class-light chain type immunoglobulins for example at higher concentrations of sFLC or intact immunoglobulin in the sample.

The Applicant realised that nephelometric and turbidimetric immunoassays could be improved by producing a competition-type assay involving a known amount of free light chain. The requirement for controlled amounts of FLC or intact immunoglobulin (in a competitive assay) increases production cost and complexity; however, the applicants consider the benefits offered for FLC measurement would justify these costs.

Accordingly, the invention provides a method of detecting free light chains (FLC) or intact immunoglobulins in a sample comprising incubating the sample with anti-FLC antibody, or heavy chain class-light chain type-specific antibodies, or fragments of such antibodies, and a known amount of FLC or intact immunoglobulin and detecting the binding of the antibody to the known amount of FLC or immunoglobulin.

Typically, the method comprises the steps of:
(i) mixing the serum sample with anti-FLC antibody, or heavy chain class-light chain type-specific antibodies, or a fragment thereof;
(ii) incubating the serum sample with the anti-FLC antibody or heavy chain class-light chain type-specific antibodies, or fragments thereof to form an incubated mixture;
(iii) measuring the optical absorbance or scattering of a light source, of the incubated mixture to produce a control (or "base-line) reading;
(iv) mixing a predetermined amount of particles coated with a known amount of FLC or intact immunoglobulin, with the incubated mixture;
(v) measuring the formation of complexes of the coated particles with the anti-FLC antibody or heavy chain class-light chain type-specific antibodies, or fragments thereof;
and (vi) comparing the formation of the complexes with a predetermined calibration curve of complex formation with known concentrations of FLC or intact immunoglobulin.

Typically the method is an agglutination assay, for example nephelometric or turbidimetric assay.

The anti-FLC antibody or fragment is one that is specific for binding free light chain, for example, lambda free light chain or kappa free light chain.

The heavy chain class-light chain type-specific antibodies or fragments may be IgA, IgG, IgM, IgD or IgE specific (typically IgA specific), and additionally lambda or kappa type specific. The antibodies may also be subclass specific, for example, anti-IgA (IgA1 and IgA2) and anti-IgG (such as IgG1, IgG2, IgG3 or IgG4).

This allows for example, abnormal IgGκ and IgGλ, or IgAκ and IgAλ to be observed.

The fragments may be Fab, Fab' or $F(ab')^2$.

The sample is mixed with anti-FLC antibody or heavy chain class-light chain type-specific antibodies, to form the incubated mixture for sufficient time to allow the antibody to bind to free light chains or intact immunoglobulins within the sample. Typically this will be approximately 5 minutes. The optical reading taken at the end of this time is used as a standard reading to eliminate the effects of any complex that is formed between the free light chain in the sample and the antibody. The optical reading may be the optical absorbance or scattering of light from a light source.

Formation of complexes of the coated particles with the anti-FLC antibody or heavy chain class-light chain type-specific antibodies may be determined by, for example, measuring the optical absorbance or the scattering of a light source. The formation of the complex between the coated particles and the anti-FLC antibody or heavy chain class-light chain type-specific antibodies is typically predetermined and followed over time and compared to a calibration curve. A calibration curve is typically predetermined and constructed by measuring serum samples with known FLC or intact immunoglobulin concentrations. The greatest light scattering or absorption is produced when there is no FLC or intact immunoglobulin in the serum sample, because all of the antibody is then available to react with the coated particles. Typically the particles are coated with polyclonal FLC.

The anti-FLC antibodies and heavy chain class-light chain type-specific antibodies are typically polyclonal antibodies for example of the type commercially available under the trademarks "Freelite" and "Hevylite", available from the Binding Site Group Limited, Birmingham, United Kingdom. Methods of raising such antibodies are discussed generally in WO 97/17372 and WO 2006079816. Monoclonal antibodies might also be used.

The sample is preferably a blood, urine, more typically serum or plasma sample.

The particle may be any suitable organic or inorganic particle suitable for using with the method of the invention, for example the inorganic material may be carbon. silica, gold or iron oxide. The organic material may be polymeric, for example polystyrene, polyvinylchloride, polyvinylidene chloride, one or more epoxy resins, or other polymers known in the art and copolymers thereof. The use of polystyrene spheres is also known as "latex enhancement". Typically the particles have sizes from 30-600 nm.

The principles of nephelometry and turbidimetric assaying are generally known in the art.

The polyclonal FLC will usually be intact FLC. However, it is also intended that this term should include the possibility of utilising fragments of FLC, providing they are still antigenic to the anti-FLC antibody.

The known amount of intact immunoglobulin (that is having light chains bound to heavy chains) is typically a predetermined heavy chain class-light chain type, for example, IgGκ, IgGλ, IgAκ or IgAλ, to which the antibody is specific. Fragments of the immunoglobulins may also be used, provided they retain heavy chain class-light chain type epitopes for the antibodies, or fragments, to specifically bind to. The intact immunoglobulin is typically polyclonal.

Competitive assays are generally avoided because of the additional costs of producing consistent batches of antigen bound to particles. This often precludes the commercial use of competitive formats. This meant that, as discussed by Angelino (see above), problems with antigen excess will usually be overcome by either dilution of the serum samples or alternatively using ELISA-type assays. The development of nephelometric/turbidimetric assays allows the measurements to be made on fully-automated laboratory analysers, alongside other immunoglobulin measurements.

The Applicants have realised that the observed differences in reaction kinetics seen between different monoclonal FLC may well be due to differences in the number and accessibility of epitopes present. Using a competition format with pre-incubation of the sample and antibody overcomes some of these differences and gives consistency of measurement. The polymerisation of FLC, such as kappa FLC, greatly accelerates the reaction kinetics of the binding of anti-FLC and leads to over-reading of the concentration. A competition assay of the type described above overcomes any over-reading due to the polymerisation of the FLC.

FLC assays are at particular risk of antigen excess problems, compared to assays for other antigens because of the massive range of concentrations found in clinical samples and the limited number of epitopes present on some monoclonal FLCs. The competition assay described above removes the possibility of antigen excess.

Such advantages also apply to the heavy chain class-light chain assays.

This improved assay allows the improved detection of monoclonal FLC or heavy chain class-light chain type intact immunoglobulins, while still using existing nephelometric and turbidimetric devices.

The inventors have also identified a method of increasing the availability of the FLC-specific epitopes of the FLC attached to the coated particles. Such epitopes are normally hidden when light chains are bound to heavy chains.

By attaching a linker to light chains bound to heavy chains and then removing the heavy chains to expose the FLC-specific epitopes, it is possible to link the separated light chain to the particle at the part of the light chain exposed to the linker in the intact light chain-heavy chain tetramer. This leaves the FLC-specific epitopes available for antibody binding once the light chains and heavy chains have become dissociated.

The invention provides a method of attaching a free light chain to a substrate, such as a particle, comprising:
(i) attaching a linker moiety to light chains attached to heavy chains
(ii) dissociating and separating the heavy chains and light chains comprising the linker moiety and
(iii) isolating light chains attached to the substrate.

The light chains may be directly attached to the substrate prior to dissociation, for example if the linker is already attached to the substrate, or indirectly attached. For example, the linker moiety may be attached via a separated binding moiety provided on the substrate which binds to the linker moiety.

The inventors have realised, for example, that a linker moiety such as biotin, can be used to biotinylate light chains whilst still attached to heavy chains, leaving biotin on the outside of the light chain away from the surface of the light chain in contact with the heavy chain (where the FLC-specific epitopes are). The heavy chain and light chains may be dissociated and separated to leave light chain with a linker moiety attached to it. The linker can then be reacted with the substrate to attach the free light chain on to the substrate. If biotin is used as the linker moiety, then avidin or streptavidin may be used to attach the free light chain to the substrate via a avidin/streptavidin-biotin binding pair.

Streptavidin-biotin is generally known in the art. The biotinylation of the light chains may be carried out using techniques generally known for the biotinylation of proteins. For example, techniques are generally known in the art to biotinylate amines and carboxylates of proteins. N-hydroxysuccinimide (NHS)-biotin may be used to attach biotin to lysine side chains. Carbodiimide cross linkers may be used to attach biotin onto carboxylate groups on glutamate and carboxylate.

Non-specific biotinylation of proteins is also generally known using commercially available photoactivatable biotinylation agents.

The substrate may be any substrate but is typically a particle as described above.

Substrates, such as particles, obtainable by the methods described above are also provided.

Kits containing such particles and their use in the methods of assay of the invention are also provided.

Alternatively a hapten antibody linker may be used.

Assay kits for use in the method of the invention comprising particles coated with a known amount of FLC or heavy chain class-light chain type intact immunoglobulins are provided. Particles and or heavy chain class-light chain intact immunoglobulins or FLC may be as described above. The kits may comprise one or more buffers or other reagents.

The kits may additionally comprise a predetermined amount of anti-FLC antibody or heavy chain class-light chain type -specific antibodies or fragments thereof, as described above.

The invention will now be described by way of example only with reference to the following figures:

FIG. 1 schematic representation of antibodies binding to latex bond antigen.

FIG. 6 shows an example of a calibration curve for kappa FLC used to determine kappa FLC values, in serum samples, for a correlation with prior art assays which do not use the particle-based kappa.

FIG. 7 shows a linear regression plot for kappa FLC comparing the method versus the prior art.

FIG. 8 shows an example of a calibration curve for lambda FLC used to determine lambda FLC values, in serum samples, for a correlation with prior art assays which do not use particle-based lambda.

FIG. 9 shows a linear regression plot for lambda FLC comparing the method versus the prior art.

Figure 1:
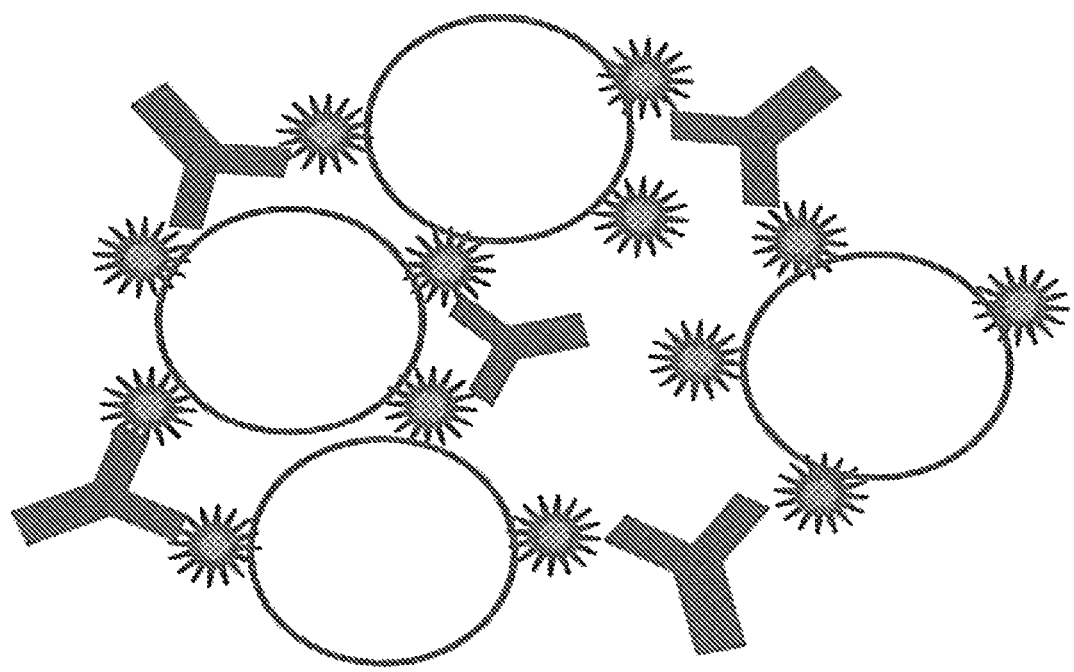

Free Light Chain Particle Enhanced Turbidimetric Inhibition Immunoassay

Reagent Composition and Manufacture

R1 Reagent

This buffer, referred to as the 'reaction buffer', consists of 100 mM PBS (phosphate buffered saline). Present in this buffer is F(ab)2 antibody ("Freelite" from The Binding Site Group Limited, Birmingham, United Kingdom), at a typical titre of less than 50 mg/L. An accelerant may be used. The accelerant is polyvinylpyrrolidone at less than 2% w/w. 25 mM Tris may also be used as a buffer. Whole antibody may also be used.

R2 Reagent

This may consist of an antigen bound to chloromethyl polystyrene particles of a given size, blocked with the presence of a detergent, such as Tween20 (polysorbate 20). Chloromethyl beads ("latex") are suspended in the coupling buffer, 25 mM MES 2-(N-morpholino)ethinesulfonic acid), and to this is added a specified amount of antigen, with the resulting mixture incubated overnight at 37° C. The following day, this is centrifuged for 20 minutes at 8,000 RPM, the supernatant discarded, and the beads re-suspended by sonication in the block buffer, which consists of 0.1M GBS (glycine buffered saline) containing a set amount of Tween20. The centrifuge step is then repeated and the beads re-suspended into fresh block buffer. The reagent is then diluted by a set dilution to give the working reagent.

An alternative way of producing them is to use carboxyl modified latex beads of a given size that are covalently linked to streptavidin by the carbodiimide EDAC in 25 mM MES 2-(N-morpholino)ethinesulfonic acid), and blocked with the addition of bovine serum albumin. The beads are then washed into 0.1M GBS (glycine buffered saline) by centrifugation. Biotinylated antigen (biotinylated at varying protein: biotin ratios) is then coated onto the beads and any remaining unbound streptavidin sites quenched with the addition of free biotin. The beads are then washed into further 0.1M GBS and diluted with water to give working reagent with typical latex bead solids content of 0.133% (g/100 g). The results described below use reagent made by this process.

Assay Principle and Reaction Sequence

R1 reagent enters a reaction cuvette and is mixed with sample. There is a period of incubation before the addition of R2 reagent and this has been termed the 'pre-reaction'. During this pre-reaction, any antigen present in the sample is able to react with the F(ab)2 antibody and form immune complexes. Because of the scarcity of the antigen, small immune complexes are formed that are not detected by standard instrumentation which uses a wavelength unable to detect complexes of this size. The addition of the R2 reagent means any remaining antibody is used to cross link the polystyrene bead and form complexes large enough to be detected at the utilized wavelength. Therefore, the more antigen present in the sample, the less signal is generated, meaning that change in signal is inversely proportional to the presence of antigen. This concept is represented schematically in the following diagrams:

FIG. 1. There is no antigen present in sample and all antibody is used to cross link latex bound antigen, resulting in a high amount of signal.

Figure 2:
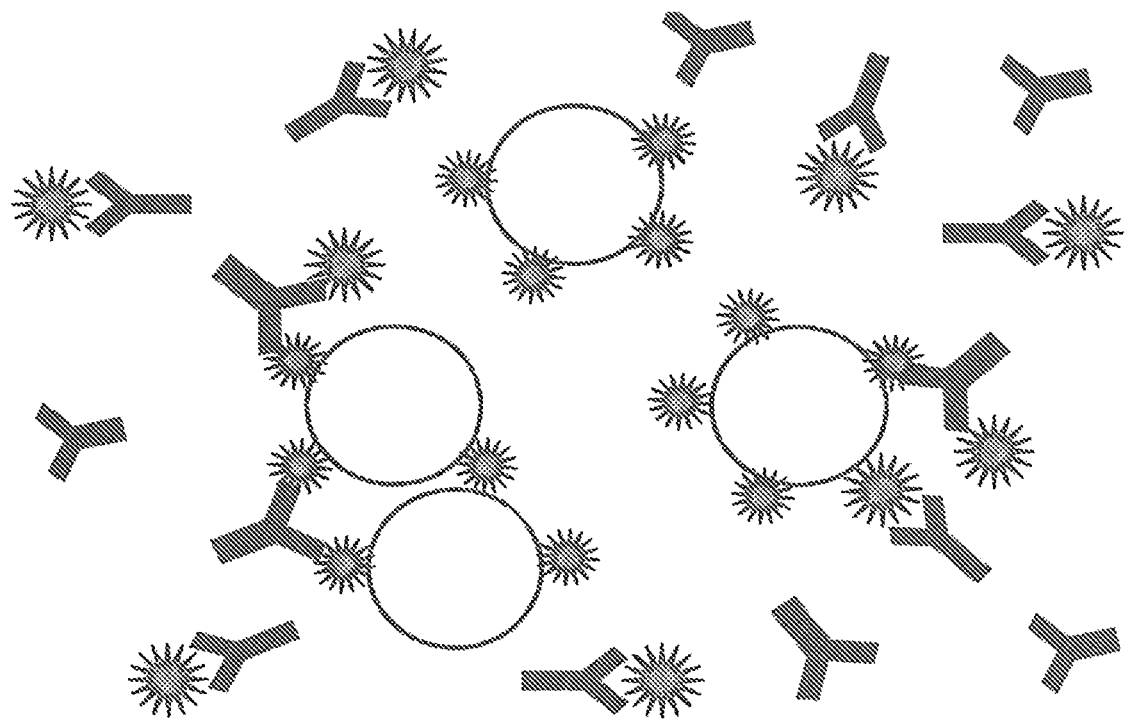
FIG. 2 shows the addition of small amounts of antigen.

FIG. 2. The addition of small amounts of antigen in the sample means antibody is 'capped' in the first reaction and is unable to cross link the bead, reducing the amount of signal generated.

Figure 3:
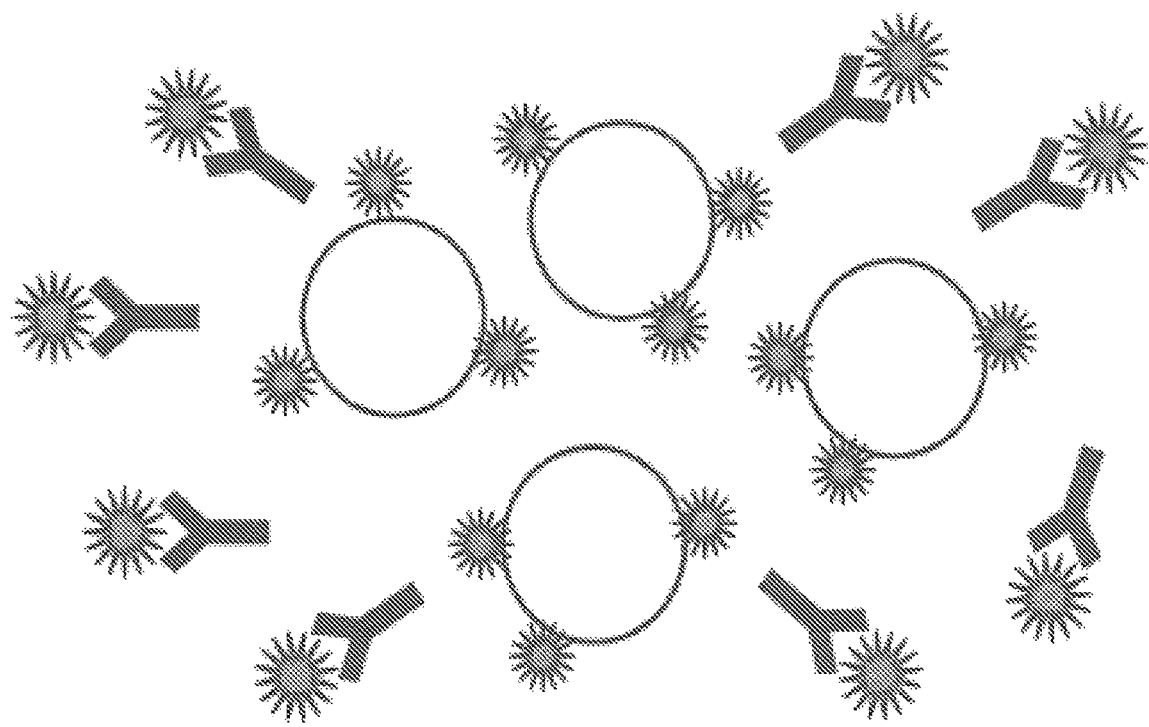
FIG. 3 shows the addition of large amounts of antigen.

FIG. 3. The addition of large amounts of antigen in the sample causes all antibody to be capped in the first reaction. No antibody is left to be able to cause cross linkage of the bead, and no change in signal occurs.

Figure 4:
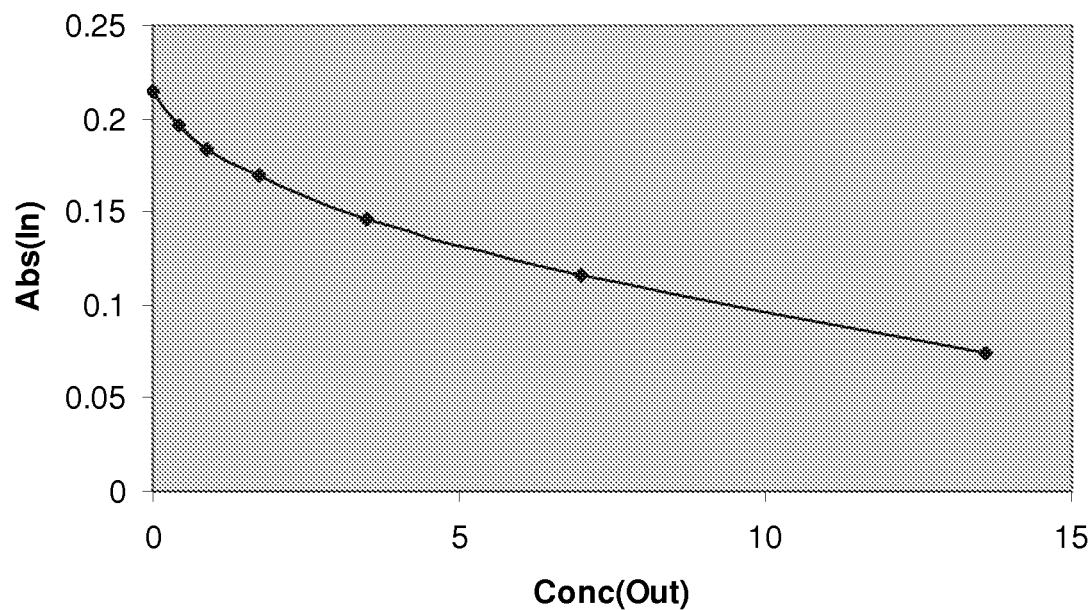
FIG. 4 shows a calibration curve for free kappa FLC using kappa FLC bound to particles.

FIG. 4 shows a calibration curve for kappa FLC using kappa FLC bound to particles. The precision data below shows the reproducibility of the assay at high and low range.

|  | Low level | High level |
| --- | --- | --- |
| 1 | 0.743 | 9.211 |
| 2 | 0.728 | 9.401 |
| 3 | 1.051 | 10.042 |
| 4 | 1.212 | 10.059 |
| 5 | 0.617 | 9.939 |
| 6 | 0.836 | 10.048 |
| 7 | 0.680 | 10.321 |
| 8 | 0.740 | 9.726 |
| 9 | 0.877 | 9.496 |
| 10 | 0.597 | 9.822 |
| SD | 0.19 | 0.35 |
| Mean (mg/L) | 0.81 | 9.81 |
| CV | 24.07% | 3.54% |

Figure 5:
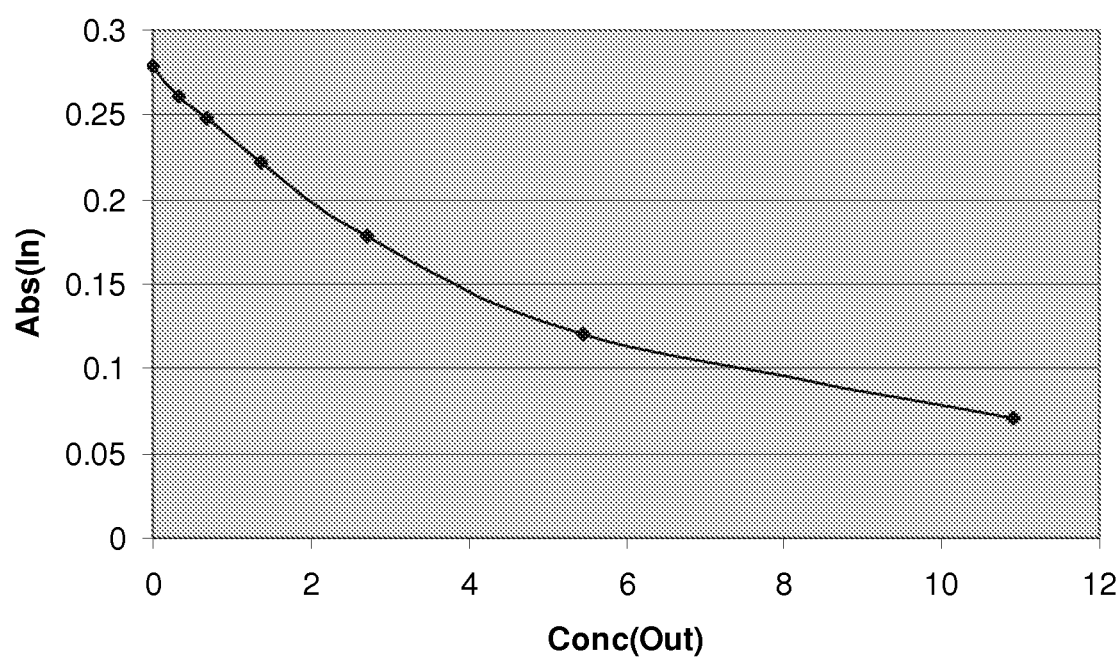
FIG. 5 shows a calibration curve for free lambda FLC using lambda FLC bound to particles.

FIG. 5 shows a calibration curve for lambda FLC using lambda FLC bound to lambda particles. Precision data for the assay is shown below.

|  | Low level | High level |
| --- | --- | --- |
| 1 | 0.58 | 7.30 |
| 2 | 0.57 | 6.99 |
| 3 | 0.76 | 7.63 |
| 4 | 0.71 | 7.02 |
| 5 | 0.54 | 6.99 |
| 6 | 0.53 | 7.01 |
| 7 | 0.57 | 7.54 |
| 8 | 0.68 | 7.08 |
| 9 | 0.54 | 7.04 |
| SD | 0.08 | 0.25 |
| Mean (mg/L) | 0.61 | 7.18 |
| CV | 13.95% | 3.49% |

FIGS. 6 and 8 show calibration curves which have been used to determine kappa and lambda FLC values respectively, for the same serum samples, to show correlation with prior art assays. Although calibrators have not been fully assigned, the values correlate very well with values determined using prior art assays (kappa $R^2$=0.66, lambda $R^2$=0.78) FIGS. 7 & 9. The high $R^2$ values show that it is the same parameter that is being analysed and considering both the kappa and lambda FLC correlations together indicates both a good sensitivity and good specificity for the assay method.

What is claimed is:

1. A method of detecting free light chains (FLC) or intact immunoglobulins in a sample comprising incubating the sample with anti-FLC antibody, or heavy chain class-light chain type-specific antibodies, or fragments of such antibodies, and a known amount of FLC or intact immunoglobulin and detecting the binding of the antibody to the known amount of FLC or immunoglobulin, characterized in that the method comprises the steps of:
   (i) mixing the sample with anti-FLC antibody, a heavy chain class-light chain type-specific antibody, or a fragment of the anti-FLC antibody or the heavy chain class-light chain type-specific antibody:
   (ii) incubating the sample with the anti-FLC antibody, the heavy chain class-light chain type-specific antibody, or the fragment of the antibody to form an incubated mixture;
   (iii) measuring the optical absorbance or scattering of a light source of the incubated mixture to produce a control reading;
   (iv) mixing a predetermined amount of particles coated with a known amount of FLC or intact immunoglobulin with the incubated mixture;
   (v) measuring the formation of complexes of the coated particles with the anti-FLC antibody, the heavy chain class-light chain type-specific antibody, or a fragment of the anti-FLC antibody or the heavy chain class-light chain type-specific antibody; and
   (vi) comparing the formation of the complexes with a predetermined calibration curve of complex formation with known concentrations of FLC or intact immunoglobulin.

2. The method according to claim 1, wherein the particles are polystyrene microparticles.

3. The method according to claim 2, wherein the particles are coated with polyclonal FLC.

4. The method according to claim 1, wherein the sample is a serum sample, a plasma sample, or a urine sample.

5. The method according to claim 4, wherein the method is a nephelometric assay or a turbidimetric assay.

6. The method according to claim 4, wherein the fragment of the antibody is selected from Fab, Fab' or F(ab')$_2$ and is capable of specifically binding to FLC.

7. The method according to claim 4, wherein the anti-FLC antibody or the fragment of the antibody is capable of specifically binding to λ FLC or FLC.

8. A method of preparing FLC-coated particles, comprising:
   (i) attaching a linker moiety onto a plurality of light chains, wherein the plurality of light chains are further attached to a plurality of heavy chains of immunoglobulins,
   (ii) dissociating the plurality of light chains comprising the linker moiety from the plurality of heavy chains of the immunoglobulins to produce FLC,
   (iii) isolating the FLC via the linker moiety, wherein the linker is attached to the particles.

9. The method according to claim 8, wherein the linker moiety comprises biotin.

* * * * *